(12) United States Patent
Seo et al.

(10) Patent No.: US 6,616,941 B1
(45) Date of Patent: Sep. 9, 2003

(54) POLYMERIC COMPOSITION FOR SOLUBILIZING POORLY WATER SOLUBLE DRUGS AND PROCESS FOR THE PREPARATION THEREOF

(75) Inventors: Min-Hyo Seo, Daejeon (KR); In-Ja Choi, Daejeon (KR)

(73) Assignee: Samyang Corporation, Seoul (KR)

( * ) Notice: Subject to any disclaimer, the term of this patent is extended or adjusted under 35 U.S.C. 154(b) by 0 days.

(21) Appl. No.: 09/807,487

(22) PCT Filed: Aug. 10, 2000

(86) PCT No.: PCT/KR00/00885
§ 371 (c)(1),
(2), (4) Date: Jul. 13, 2001

(87) PCT Pub. No.: WO01/12718
PCT Pub. Date: Feb. 22, 2001

(51) Int. Cl.[7] .............................................. A61K 9/127
(52) U.S. Cl. ...................... 424/450; 424/427; 424/435; 424/449; 424/486; 424/78.18; 424/78.22; 424/78.23
(58) Field of Search ............................. 424/450, 78.18, 424/78.22, 78.23, 427, 435, 449, 486

(56) References Cited

U.S. PATENT DOCUMENTS

| 5,429,826 A | 7/1995 | Nair et al. |
| 5,449,513 A | 9/1995 | Yokoyama et al. |
| 5,665,428 A | 9/1997 | Cha et al. |
| 5,702,717 A | 12/1997 | Cha et al. |

FOREIGN PATENT DOCUMENTS

| EP | 0921 139 A1 | 6/1999 |
| KR | 99069033 | 9/1999 |
| WO | WO95/10265 | 4/1995 |

OTHER PUBLICATIONS

X. Zhang, et al., Int. J.Pharm 132 (1996) 195–206.

I. Gyun Shin, et al., J. Contr. Red., 51 (1998) 13–22.

Primary Examiner—Jyothsan Venkat
(74) Attorney, Agent, or Firm—Thorpe North & Western, LLP

(57) ABSTRACT

A composition capable of forming a micelle in body fluids or in an aqueous medium and that can be injected into the body undiluted or as a diluted solution in an aqueous medium and method of preparation are disclosed. The composition comprises an amphiphilic block copolymer having a hydrophilic poly(alkyleneglycol) component and hydrophobic biodegradable polymer component, suspended in a poly (alkyleneglycol) medium. Such composition is used in the solubilization and administration of a poorly water-soluble drug.

16 Claims, No Drawings

POLYMERIC COMPOSITION FOR SOLUBILIZING POORLY WATER SOLUBLE DRUGS AND PROCESS FOR THE PREPARATION THEREOF

This application is a 371 of PCT/KR00/00885 filed on Aug. 10, 2000.

TECHNICAL FIELD

The present invention relates to a biodegradable polymeric composition containing a block copolymer having a hydrophilic poly(alkylene glycol) component and a hydrophobic biodegradable polymer component suspended in a poly(ethylene glycol) medium, and to a method for the preparation thereof. The composition can effectively solubilize a hydrophobic drug and forms a solution which can be stored as a stable liquid formulation. Furthermore, the composition can be injected into the body undiluted or as a diluted solution in an aqueous medium, and therefore is useful for the intravenous administration of poorly water soluble drugs.

BACKGROUND ART

Many important drugs are hydrophobic and have limited solubility in water. In order to attain the expected therapeutic effect from such drugs, it is usually required that a solubilized form of the drug be administered to a patient. Therefore, solubilization of a poorly water soluble drug is key technology in the preparation of a formulation for oral or parenteral, especially intravenous, administration of the drug. Common methods used for solubilization of poorly water soluble drugs are: i) dissolving the drug in a co-solvent of a water-miscible organic solvent and water; ii) modifying the drug as a salt that can be soluble in water; iii) forming a soluble drug-complex using a complexing agent; and iv) micellizing the drug in an aqueous medium with a surfactant. (Leon Lachman, "The Theory and Practice of Industrial Pharmacy", Lea & Febiger, Philadelphia, 1986).

Solubilization methods using surfactants without requiring any changes in the chemical structure of a drug has been widely used to solubilize various drugs. Non-ionic surfactants, eg. polyoxyethylene sorbitan fatty acid esters (Tween®) and polyoxyethylene alkyl ethers(Brij™ or Myrj™), are commonly used as the surface active agents. European Patent EP 0645145 discloses a method of solubilizing a typical poorly water soluble drug, paclitaxel, by use of Cremophor EL™, a polyoxyethylene castor oil derivative. The use of these surfactants, however, is restricted due to their toxic side effects such as hypersensitivity, and they have limitations in that their poor ability to stabilize micelles can cause precipitation of the drug when the micellar solution is either stored or is to remain in place for an extended period of time.

Other solubilization methods using a polymeric micelle, wherein the polymer is a diblock or triblock copolymer consisting of a hydrophilic poly(alkylene glycol) derivative and a hydrophobic biodegradable aliphatic polyester or poly(amino acid), has been developed (see U.S. Pat. Nos. 5,449,513 and 5,429,826). However, poly(amino acid) derivatives or other crosslinked polymers used in the formation of polymeric micelles, cannot be hydrolyzed or degraded in the body, which can cause undesired immune reactions.

X. Zhang et al. reported that a polymeric micelle prepared with a diblock copolymer of poly(lactic acid) and monomethoxy poly(ethylene glycol) was useful as a carrier of paclitaxel. (X. Zhang et al., Int. J. Pharm. 132(1996) 195–206), and Shin et al. disclose a solubilization method for indomethacin using a diblock copolymer of poly (ethylene glycol) and polycaprolactone(I. Gyun Shin et al., J. Contr. Rel., 51(1998) 13–22). In these methods, a poorly water soluble drug is incorporated in a polymeric micelle, wherein the polymers are biocompatible and biodegradable. According to their methods, a drug and a block copolymer are dissolved together in an organic solvent, especially in a water-miscible organic solvent such as tetrahydrofuran or dimethyl formamide. The polymeric micelles are prepared by dialyzing the solution in water first and then freeze-drying the aqueous micellar solution. Alternatively, a solution of a polymer and drug in a water-miscible organic solvent, acetonitrile, is prepared. The organic solvent is slowly evaporated to give a homogeneous drug-polymer matrix and the matrix is then dispersed in an aqueous medium at ca. 60° C. to form the polymeric micelles.

As described above, a conventional solubilizing method for a poorly water soluble drug using polymeric micelles employs complicated steps including formation of an aqueous polymeric micellar solution containing a poorly water soluble drug, followed by preparation of a freeze-dried powder. Moreover, the powdered product must then be reconstituted when used in a hospital or other setting and it is not possible to store the product in an aqueous solution because of the hydrolyzable and biodegradable component in the polymer. Another disadvantage is that this method cannot be applied to a polymer having a melting temperature below about 50° C.

DISCLOSURE OF THE INVENTION

The present invention provides a composition capable of forming a micelle in body fluids or in an aqueous medium and that can be injected into the body in neat or undiluted form or in diluted form as an aqueous solution. The present invention also provides a composition capable of solubilizing a poorly water soluble drug and a method for the preparation thereof.

The composition of the present invention comprises a block copolymer of a hydrophilic poly(alkylene glycol) block and a hydrophobic biodegradable polymer block dispersed or suspended in a poly(ethylene glycol) matrix or its derivatives. The term poly(ethylene glycol) or PEG, as used herein, shall also be deemed to include derivatives of PEG unless otherwise specifically stated. Such derivatives will be more specifically described in the disclosure that follows. Since only the hydrophilic component block, not the hydrophobic component block, of the copolymer has an affinity or attraction for the poly(ethylene glycol) matrix, the block copolymer forms a core-shell structure wherein the hydrophobic biodegradable polymer block occupies the inner core and the hydrophilic poly(alkylene glycol) block forms the outer shell in the poly(ethylene glycol) medium.

Preferably, the block copolymer content in the composition of the invention is within the range of 5~95 wt %, and more preferably within the range of 10~50 wt %, and the content of the water soluble poly(ethylene glycol) is within the range of 5~95 wt %, and more preferably 50~90 wt %. In a composition containing a poorly water soluble drug, the drug content is preferably within the range of 0.1~50 wt %, and more preferably 5~30 wt % based on the weight of the block copolymer.

A biocompatible water-miscible organic solvent may be added into the composition of the present invention to facilitate better solubility of a drug. The added amount of the organic solvent depends on the solubility of a drug, and preferred content of the solvent is less than 50 wt % based on the amount of poly(ethylene glycol) or its derivatives. The present invention is described in detail hereinafter.

BEST MODE FOR CARRYING OUT THE INVENTION

The present invention is directed to a composition containing an amphiphilic block copolymer having a hydrophilic poly(alkylene glycol) component and a hydrophobic biodegradable polymer component dispersed or suspended in a poly(ethylene glycol) medium, and to a method for the preparation thereof.

The combined block copolymer and poly(ethylene glycol) composition is a liquid that is shelf stable over extended periods of time. The block copolymer portion of such compositions have a core-shell structure in the poly(ethylene glycol) medium wherein the hydrophobic biodegradable polymer block occupies the inner core and the hydrophilic poly(alkylene glycol) block forms the outer shell in the water soluble poly(ethylene glycol) matrix or medium. When administered, the poly(ethylene glycol) functions as a dispersant to facilitate water solubility and the block copolymer portion of the composition forms a micelle structure in body fluids or in an aqueous medium. When a drug is added to the block copolymer and poly(ethylene glycol) composition the poorly water soluble drug is contained within the inner hydrophobic core. Accordingly, a pharmaceutical formulation containing the polymer composition of the present invention and a poorly water soluble drug can be stored as a stable liquid formulation without degradation of the biodegradable polymer block. The formulation is capable of solubilizing effectively a poorly water soluble drug in a body fluid or in an aqueous medium by forming a micelle, wherein the drug is entrapped in the core of the micelle.

In summary, the present invention is a combination of a block copolymer, as defined herein, suspended in a poly (ethylene glycol) medium which is a liquid. The amphiphilic block copolymer of the present invention comprises a hydrophilic poly(alkylene glycol) component and a hydrophobic biodegradable polymer component. When placed in an aqueous environment, such as body fluids or fomulated as a suspension, syrup or the like, the poly(ethylene glycol) medium facilitates the dispersion of the block copolymer which forms a polymeric micelle in the aqueous medium. When a poorly water soluble drug is added to the composition and placed in an aqueous environment, the drug is solubilized by incorporating the drug into the inner core of the micelle.

The polyalkylene glycol suitable for the hydrophilic component in the block copolymer of the present invention is a member selected from the group consisting of polyethylene glycol, monoalkoxy polyethylene glycol, or monoacyloxy polyethylene glycol wherein the molecular weight of the polyalkylene glycol is preferably within the range of 200~20,000 Daltons, and more preferably within the range of 1,000~15,000 Daltons. The content of the hydrophilic component is within the range of 40~80 wt %, preferably 40~70 wt %, based on the total weight of the block copolymer.

The hydrophobic biodegradable polymer component of the copolymer of the present invention is a member selected from the group consisting of polylactides, polycaprolactone, copolymers of lactide and glycolide, copolymers of lactide and caprolactone, copolymers of lactide and 1,4-dioxan-2-one, polyorthoesters, polyanhydrides, polyphosphazines, poly(amino acid)s and polycarbonates. Preferably, the hydrophobic biodegradable polymer component of the copolymer of the present invention is a member selected from the group consisting of polylactide, polycaprolactone, a copolymer of lactide and glycolide, a copolymer of lactide and caprolactone, and a copolymer of lactide and 1,4-dioxan-2-one. The molecular weight of the hydrophobic biodegradable polymer component is preferably within the range of 500~20,000 Daltons, and more preferably within the range of 1,000~10,000 Daltons.

The amphiphilic block copolymer of the present invention may be an AB type diblock, an ABA or BAB type triblock copolymer comprising a hydrophilic poly(alkylene glycol) A-block component (A) and a hydrophobic biodegradable polymer B-block component(B), which forms a micelle in an aqueous medium, and is dissolved or mixed homogeneously in a poly(ethylene glycol) medium.

The amphiphilic block copolymers can be prepared according to methods described in U.S. Pat. Nos. 5,683,723 and 5,702,717, hereby fully incorporated by reference. For example they may be prepared via ring opening bulk polymerization of one of the cyclic ester monomers, such as lactide, glycolide, or 1,4-dioxan-2-one with monomethoxy poly(ethylene glycol) (mPEG) or poly (ethylene glycol) (PEG) in the presence of stannous octoate as a catalyst at 80~130° C. When the 1,4-dioxan-2-one is used as the monomer, the preferable reaction temperature is 80~110° C. When a copolymer of 1,4-dioxan-2-one and lactide is used, the 1,4-dioxan-2-one monomer is first reacted with mPEG or PEG at 100~130° C., the lactide monomer is then slowly added to increase the degree of polymerization of 1,4-dioxan-2-one. Since the conversion of 1,4-dioxan-2-one monomer is 50~60%, the added amount of this monomer should be more than the calculated amount when the two monomers, 1,4-dioxan-2-one and lactide, are added together. The block copolymer product is dissolved in dichloromethane or acetone, precipitated in diethyl ether, hexane, pentane, or heptane, followed by drying.

The poly(ethylene glycol) or its derivatives used as a dispersion medium for the composition of the present invention are water soluble polymers having high attraction for the hydrophilic component of the block copolymer. Preferably, the poly(ethylene glycol), or an appropriate derivative thereof, has a melting temperature of below about 70° C., and a molecular weight of 200~10,000 Daltons. The poly(ethylene glycol), including derivatives thereof, can be represented as formula I:

$$R-O-CH_2CH_2-(O\ CH_2CH_2)n-O-R \qquad [I]$$

wherein R is hydrogen, $C_1$~$C_4$ alkyl, benzyl, or acyl, and n is an integer of 3~220.

Examples of the $C_1$~$C_4$ alkyl in the formula I include methyl, ethyl, propyl, isopropyl, and butyl groups, and the acyl group includes formyl, acetyl, and benzoyl groups.

When preparing a pharmaceutical composition for IV or IM injection, a poly(ethylene glycol) having a molecular weight of 200 to 1,000 Daltons, and which can be dissolved within minutes in an aqueous medium, is preferred. When preparing a pharmaceutical composition for oral, ophthalmic, or external uses such as a patch or ointment, a poly(ethylene glycol) having a molecular weight of 1,000 to 10,000 Daltons and which can be dissolved slowly in an aqueous medium, is preferred. Any mixture of poly(ethylene glycols) having a weight average molecular weight within the above stated ranges may also be utilized.

The compositions of the present invention are especially useful for delivering poorly water soluble drugs having solubilities of less than 10 mg/mL. Examples of the hydrophobic drugs include anticancer agents, antiinflammatory agents, antifungal agents, antiemetics, antihypertensive agents, sex hormones, and steroids. Typical examples of the hydrophobic drugs are: anticancer agents such as paclitaxel, camptothecin, doxorubicin, daunomycin, cisplatin, 5-fluorouracil, mitomycin, methotrexate, and etoposide; antiinflammatory agents such as indomethacin, ibuprofen, ketoprofen, flubiprofen, diclofenac, piroxicam, tenoxicam, naproxen, aspirin, and acetaminophen; antifungal agents such as itraconazole, ketoconazole, and amphotericin; sex hormons such as testosterone, estrogen, progestone, and estradiol; steroids such as dexamethasone, prednisolone, and triamcinolone; antihypertensive agents such as captopril, ramipril, terazosin, minoxidil, and parazosin; antiemetics such as ondansetron and granisetron; antibiotics such as metronidazole, and fusidic acid; cyclosporine; and biphenyl dimethyl dicarboxylic acid.

An organic solvent, that is not an essential component in the composition of the present invention, may be added into the composition to facilitate better solubility of a drug and increase the loading efficiency into a micelle. The organic solvent employed in the composition is a polar solvent which is harmless to the body and miscible with water and poly(ethylene glycol). Examples of suitable organic solvents include ethanol, acetic acid, lactic acid, glycolic acid, N-methyl-2-pyrrolidone, benzyl alcohol, glycerin, N,N-dimethyl acetamide, propylene glycol, diethyl amine, and mixtures thereof.

The composition of the present invention may be prepared by dispersing the amphiphilic block copolymer into the poly(ethylene glycol) or its derivatives by one or more of the following methods. The composition may be first prepared without the presence of the drug or the composition may be prepared with the simultaneous incorporation of the drug.

Depending on the solubility of a hydrophobic drug in poly(ethylene glycol) or its derivatives, the composition containing a hydrophobic or a poorly water soluble drug is prepared by several methods as follows:

(1) Heating: When a poorly water soluble drug is soluble in poly(ethylene glycol), the drug and block copolymer are mixed with poly(ethylene glycol) and stirred at 30~100° C. to form a solution. The solution is then cooled to room temperature and a homogeneous drug incorporated liquid composition is obtained.

(2) Adding an organic solvent: When a poorly water soluble drug is not readily soluble in poly(ethylene glycol), the drug and block copolymer are mixed with poly(ethylene glycol) and stirred while heating. An organic solvent is added into the mixture until the drug and the block copolymer are dissolved and form a clear solution. The solution is then cooled to room temperature and a homogeneous drug incorporated liquid composition is obtained.

(3) Solvent evaporation: When a poorly water soluble drug is practically insoluble in poly(ethylene glycol), the drug, block copolymer, and poly(ethylene glycol) are dissolved together in an organic solvent having a boiling temperature of less than 100° C., such as ethanol, methanol, ethyl acetate, dichloromethane, chloroform, acetonitrile, or acetone. The organic solvent is then evaporated by heating and/or under vacuum, to yield a composition wherein the block copolymer incorporated with a drug is homogeneously dispersed in the poly(ethylene glycol)).

The composition of the present invention, which is easily dispersed in an aqueous medium, is capable of solubilizing a poorly water soluble drug in water and can be formulated as: an oral formulation such as liquid and capsule; a transdermal formulation such as an ointment or patch; and an injection fluid for intravenous, intramuscular, or subcutaneous administration. When the composition is administered by injection, it can be dissolved in an appropriate medium for injection, eg. saline or DW5, prior to use, or can be injected without dissolution. For non-injection administration, eg. oral route, the composition is formulated with pharmaceutically acceptable additives, eg. mannitol, sorbitol, hydroxypropyl cellulose, and hydroxypropyl methyl cellulose.

The composition of the present invention which, in an aqueous medium, forms a polymeric micelle, is especially suitable for the intravenous injection of a poorly water soluble anticancer agent such as paclitaxel.

The composition of the present invention can also be used as a carrier for any other poorly water soluble substances into the body as well as for poorly water soluble drugs.

While the following examples are provided for the purpose of illustrating certain aspects of the present invention, they are not to be construed as limiting the scope of the appended claims.

EXAMPLES

Example 1

Preparation of mPEG-PLA Diblock Copolymer (MW: 2,000–1,850 Daltons)

A combination of 20 g of monomethoxy polyethyleneglycol (mPEG, molecular weight(mw): 2,000) and 19 g of D,L-lactide recrystallized from ethyl acetate was added to a 100 mL round-bottomed flask equipped with a mechanical stirrer. Into the flask was added 24.5 mg of stannous octoate in 3 mL of toluene and the toluene was evaporated at an elevated temperature of 120° C. under vacuum. The reaction mixture was stirred for 6 hours at 120° C. under vacuum (25 mmHg). The resulting product was cooled to room temperature and dissolved in dichloromethane. The solution was poured into cold anhydrous ether (4° C.) to precipitate the diblock polymer that was formed. The mPEG-PLA diblock copolymer (MW: 2,000–1,850 Daltons) was purified by repeating twice the dissolution-precipitation process. (Yield: 37 g, 95%)

Example 2

Preparation of mPEG-PLA Diblock Copolymer (MW: 2,000–1,240 Daltons)

A diblock copolymer was prepared by the same method as in Example 1 using 20 g of mPEG(mw: 2,000), 12.5 g of D,L-lactide (mw: 1,240), and 20 mg of stannous octoate to form a mPEG-PLA diblock copolymer (MW: 2,000–1,240 Daltons). (Yield: 30 g, 92%)

Example 3

Preparation of mPEG-PLA Diblock Copolymer (MW: 5,000–3,790 Daltons)

A diblock copolymer was prepared by the same method as in Example 1 using 25 g of mPEG(mw: 5,000), 19 g of D,L-lactide (mw 3,790 daltons), and 10 mg of stannous octoate to form a mPEG-PLA diblock copolymer (MW: 5,000–3,790 daltons). (Yield: 42 g, 96%)

Example 4

Preparation of mPEG-PLGA Diblock Copolymer (MW: 2,000–1,720 Daltons, LA/GA=7:3)

A diblock copolymer was prepared by the same method as in Example 1 using 20 g of mPEG(mw: 2,000), 12.5 g of D,L-lactide (LA), 4.5 g of glycolide (GA), and 20 mg of stannous octoate to form a mPEG-PLGA diblock copolymer (MW: 2,000–1,720 Daltons, mole ratio of LA/GA=7:3). (Yield: 35.5 g, 96%)

Example 5

Preparation of mPEG-PDO Diblock Copolymer
(MW: 2,000–1,190 Daltons)

A diblock copolymer was prepared by the same method as in Example 1 using 20 g of mPEG(mw: 2,000), 12 g of 1,4-dioxan-2-one, and 20 mg of stannous octoate to form a mPEG-PDO diblock copolymer (MW: 2,000–1,190 Daltons). (Yield: 28.2 g, 88%)

Example 6

Preparation of mPEG-PLDO Diblock Copolymer
(MW: 2,000–1,400 Daltons, LA/DO=7:3)

A diblock copolymer was prepared by the same method as in Example 1 using 20 g of mPEG(mw: 2,000), 11 g of D,L-lactide (LA), 3.4 g of 1,4-dioxan-2-one (DO), and 20 mg of stannous octoate to form a MPEG-PLDO diblock copolymer (MW: 2,000–1,400 Daltons, mole ratio of LA/DO=7:3). (Yield: 33 g, 95%)

Example 7

Preparation of mPEG-PLDO Diblock Copolymer
(MW: 5,000–2,900 Daltons, LA/DO=7:3)

A diblock copolymer was prepared by the same method as in Example 1 using 25 g of mPEG(mw: 5,000), 11 g of D,L-lactide, 3.4 g of 1,4-dioxan-2-one, and 10 mg of stannous octoate to form a mPEG-PLDO diblock copolymer (MW: 5,000–2,900 Daltons, mole ratio of LA/DO=7:3). (Yield: 38 g, 96%)

Example 8

Preparation of mPEG-PLDO Diblock Copolymer
(MW: 5,000–4,880 Daltons, LA/DO=5:5)

A diblock copolymer was prepared by the same method as in Example 1 using 25 g of mPEG(mw: 5,000), 14.4 g of D,L-lactide (LA), 10.2g of 1,4-dioxan-2-one (DO), and 10 mg of stannous octoate to form a mPEG-PLDO diblock copolymer (MW: 5,000–4,880 Daltons, mole ratio of LA/DO=5:5). (Yield: 46 g, 93%)

Example 9

Preparation of mPEG-PCL Diblock Copolymer
(MW: 2,000–1,720 Daltons,)

A diblock copolymer was prepared by the same method as in Example 1 using 20 g of mPEG(mw: 2,000), 17 g of caprolactone (CL), and 20 mg of stannous octoate to form a mPEG-PCL diblock copolymer (MW: 2,000–1,720 Daltons). (Yield: 36 g, 97%)

Example 10

Preparation of mPEG-PLA-mPEG Triblock
Copolymer

A solution of 10 g (2.6 mmole) of the diblock copolymer prepared in Example 1 and 210 mg (1.36 mmole) of succinyl chloride dissolved in 50 mL toluene was added to a 100 mL round-bottomed flask equipped with a mechanical stirrer. The solution was refluxed for 6 hours at 110~130° C., and then, toluene was evaporated at 120° C. under vacuum. The product was cooled down to a room temperature and diluted in hexane to separate the polymer. The polymer was dissolved in dichloromethane, precipitated in cold anhydrous ether, and dried under vacuum (40° C., 1 mmHg). (Yield: 9.7 g, 96%)

Example 11

Preparation of mPEG-PLDO-mPEG Triblock
Copolymer

A triblock copolymer was prepared by the same method as in Example 10 using 10 g (2.94 mmole) of the diblock copolymer prepared in example 6 and 250 mg (1.48 mmole) of hexamethylene diisocyanate. (Yield: 10.2 g, 99%)

Example 12

Solubilization of a Poorly Water Soluble Drug

Liquid polymeric compositions were prepared using the block copolymers prepared in Examples 1~11, poorly water soluble drugs, poly (ethylene glycol), and organic solvents, when applicable, by the following methods.

(1) Heating: (Method H) A block copolymer prepared in Examples 1~11 and a poorly water soluble drug were mixed in poly (ethylene glycol), and stirred at 80° C. to give a solution. The solution was then cooled to room temperature and a homogeneous liquid composition was obtained.

(2) Adding organic solvent: (Method A) A block copolymer prepared in Examples 1~11 and a poorly water soluble drug were added into a solution of an organic solvent and poly(ethylene glycol), and stirred at 80° C. to give a solution. The solution was then cooled to room temperature and a homogeneous liquid composition was obtained.

(3) Solvent evaporation: (Method S) A block copolymer prepared in examples 1~11, a poorly water soluble drug, and poly(ethylene glycol) were dissolved in an organic solvent, and the solvent was evaporated at 40~60° C. under nitrogen flow. A homogeneous solution was obtained.

Comparative compositions were prepared without the block copolymers by the same methods described above.

The compositions prepared by the above methods are shown in Table 1. The block copolymer used is designated by block formula, molecular weight of each block and the amount of the block copolymer used. The poorly water soluble drug is listed along with the amount used. The hydrophilic PEG polymer is listed by molecular weight and amount used. The "Solvent" column is applicable to Method A and lists the solvent and the amount used. Finally, the "Method" column lists the method used and when Method S is used lists the solvent that was evaporated.

TABLE 1

Compositions containing Poorly Water Soluble Drugs

| No. | Block Copolymer | Drug | Hydrophilic Polymer | Solvent | Method* |
|---|---|---|---|---|---|
| 1 | mPEG-PLA(2,000–1,850) 270 mg | Indomethacin 30 mg | PEG 400 500 mg | — | H |
| 2 | mPEG-PLA(2,000–1,850) 285 mg | Indomethacin 15 mg | PEG 400 500 mg | — | H |
| 3 | mPEG-PLA(2,000–1,850) 240 mg | Indomethacin 60 mg | PEG 400 500 mg | — | H |
| 4 | mPEG-PLA(2,000–1,850) 270 mg | Paciltaxel 30 mg | PEG 600 400 mg | Ethanol 100 mg | A |
| 5 | mPEG-PLGA(2,000–1,720, LA/GA = 7/3) 270 mg | Cyclosporine A 30 mg | PEG 300 900 mg | Acetic acid 100 mg | A |
| 6 | mPEG-PLA(2,000–1,850) 270 mg | Dexamethasone 30 mg | dimethoxy PEG 400 1,300 mg | N-methyl-2-pyrrolidone 400 mg | A |
| 7 | mpEG-PLA(5,000–3,790) 270 mg | Doxorubicin 30 mg | diacetyl PEG 600 600 mg | Glycerin 400 mg | A |
| 8 | mPEG-PLDO(2,000–1,400, LA/DO-7/3) 90 mg | Paciltaxel 10 mg | PEG 600 200 mg | — | H |
| 9 | mPEG-PLDO(5,000–4,880, LA/DO = 5/5) 90 mg | Camptothecin 10 mg | PEG 400 500 mg | — | S (dichloromethane) |
| 10 | mPEG-PLA(2,000–1,240) 270 mg | Tenoxicam 30 mg | PEG 400 1,000 mg | — | S (dichloromethane) |
| 11 | mPEG-PLA(5,000–3,790) 270 mg | Biphenyl dimethyl dicarboxylic acid 30 mg | PEG 400 600 mg | N-methyl-2-pyrrolidone 400 mg | A |
| 12 | mPEG-PLA(2,000–1,850) 270 mg | Testosterone 30 mg | PEG 1,000 800 mg | Ethanol 200 mg | A |
| 13 | mPEG-PDO(2,000–1,190) 270 mg | Paciltaxel 30 mg | PEG 2,000 800 mg | — | S (acetonitrile) |
| 14 | mPEG-PCL(2,000–1720) 270 mg | Cyclosporine A 30 mg | PEG 6,000 800 mg | — | S (ethanol) |
| 15 | mPEG-PLA-mPEG(2,000–3,700–2,000) 270 mg | Indomethacin 30 mg | PEG 8,000 800 mg | — | S (acetonitrile) |
| C1** | — | Indomethacin 30 mg | PEG 400 800 mg | — | H |
| C2** | — | Paciltaxel 30 mg | PEG 400 800 mg | — | A |
| C3** | — | Paclitaxel 30 mg | PEG 2,000 800 mg | — | S (acetonitrile) |
| C4** | — | Testosterone 30 mg | PEG 8,000 800 mg | — | S (dichloromethane) |

*H: Heating; A: Adding organic solvent; S: Solvent evaporation
**Comparative composition Solubility of the Compositions Into a series of tubes, each containing a composition listed in Table 1, was added 1.0 mL of distilled water. The resulting mixtures were shaken by hand to facilitate micelle formation by the dissolution of the liquid polymeric composition into the aqueous medium. The mixture was then ultracentrifuged (10,000× g) for 20 minutes. The supernatant was filtered through a 0.22 μm PVDF syringe filter. The filtrate wasassayed by HPLC to determine the drug content incorporated in the micelles. The results are shown in Table 2.

TABLE 2

| | Loading Efficiency and Solubility | |
|---|---|---|
| No. | Loading Efficiency* (%) | Solubility (mg/mL) |
| 1 | 100 | 30 |
| 2 | 100 | 15 |
| 3 | 100 | 60 |
| 4 | 100 | 30 |
| 5 | 100 | 30 |
| 6 | 100 | 30 |
| 7 | 100 | 30 |
| 8 | 100 | 10 |
| 9 | 100 | 10 |

| | | |
|---|---|---|
| 10 | 100 | 30 |
| 11 | 100 | 30 |
| 12 | 100 | 30 |
| 13 | 100 | 30 |
| 14 | 100 | 30 |
| 15 | 100 | 30 |
| C1** | — | 0.001 |
| C2** | — | 0.008 |
| C3** | — | 0.010 |
| C4** | — | 0.002 |

*Loading Efficiency (%) = Solubilized drug(g)/Added drug(g) X100, where solubilized drug is asssayed by HPLC
**Comparative composition The results shown in Table 2 indicate that compositions prepared according to the present invention significantly increase solubility of a hydrophobic drug compared to compositions containing no block copolymers. Comparative compositions containing a block copolymer having a hydrophilic poly(alkylene glycol) component and a hydrophobic biodegradable polymer component and a hydrophobic drug, but no PEG were also prepared but failed to form solutions.

Therefore, the above clearly shows that the composition according to the present invention can effectively solubilize a hydrophobic drug and forms a solution. While not specifically demonstrated, such solutions can be stored as a stable liquid formulation. Furthermore, the composition can be injected into the body undiluted or as a diluted solution in an aqueous medium, and therefore is useful for the intravenous administration of poorly water soluble drugs.

While the invention has been described with respect to the above specific embodiments, it should be recognized that various modifications and changes may be made to the invention by those skilled in the art which also fall within the scope of the invention as defined by the appended claims.

We claim:

1. A composition capable of forming a polymeric micelle in a body fluid or an aqueous medium, said composition comprising an amphiphilic block copolymer having a hydrophilic poly(alkylene glycol) A block component and hydrophobic biodegradable polymer B block component, said amphiphilic block copolymer being suspended in a liquid poly(ethylene glycol) medium wherein the poly (ethylene glycol) is represented by the formula:

R—O—CH$_2$ CH$_2$—(O CH$_2$ CH$_2$)$_n$—O—R wherein R is hydrogen, C$_1$–C$_4$ alkyl, benzyl, or acyl; and n is an integer of 3–220, wherein the poly (ethylene glycol) has an average molecular weight in the range of 200 to 10,000 Daltons.

2. The composition of claim 1, wherein the block copolymer is within the range of 5 to 95 wt %, and the poly (ethylene glycol) medium is within the range of 5 to 95 wt % based on the total weight of said composition.

3. The composition of claim 1, wherein the amphiphilic block copolymer is selected from the group consisting of AB diblock, ABA triblock and BAB triblock copolymers.

4. The composition of claim 3, wherein the amphiphilic block copolymer is selected from the group consisting of AB diblock and ABA triblock copolymers.

5. The composition of claim 1, wherein the hydrophilic A block component is within the range of 40 to 80 wt % based on the total weight of the block copolymer.

6. The composition of claim 1, wherein the hydrophilic poly(alkylene glycol) A block component is poly(ethylene glycol) or monomethoxy poly(ethylene glycol).

7. The composition of claim 6, wherein the hydrophilic poly(alkylene glycol) has an average molecular weight in the range of 1,000 to 15,000 Daltons.

8. The composition of claim 1, wherein the hydrophobic biodegradable polymer B block component is selected from the group consisting of polylactide, copolymer of lactide and glycolide, copolymer of D,L-lactide and glycolide, polycaprolactone, polyanhydride, polyorthoester, copolymer of lactide and 1,4-dioxan-2-one, and copolymer of caprolactone and 1,4-dioxan-2-one.

9. The composition of claim 8, wherein the hydrophobic biodegradable polymer, has an average molecular weight in the range of 1,000 to 10,000 Daltons.

10. A hydrophobic drug containing biodegradable polymeric composition capable of solubilizing said hydrophobic drug in a hydrophilic environment to form a solution, said composition comprising a hydrophobic drug physically entrapped within but not covalently bound to a biodegradable polymeric drug carrier comprising an amphiphilic block copolymer having a hydrophilic poly(alkylene glycol) component and hydrophobic biodegradable polymer component being suspended in a poly(ethylene glycol) medium wherein the poly (ethylene glycol) is represented by the formula:

R—O—CH$_2$ CH$_2$—(O CH$_2$ CH$_2$)$_n$—O—R wherein R is hydrogen, C$_1$–C$_4$ alkyl, benzyl, or acyl; and n is an integer of 3–220, wherein the poly (ethylene glycol) has an average molecular weight in the range of 200 to 10,000 Daltons.

11. The composition of claim 10, wherein the hydrophobic drug is in the range of 0.1 to 50 wt % based on the total weight of the block copolymer.

12. The composition of claim 10, wherein the hydrophobic drug has a solubility of less than 10 mg/mL.

13. The composition of claim 12, wherein the hydrophobic drug is selected from the group consisting of anticancer agents, antifungal agents, steroids, antiinflammatory agents, sex hormones, immunosuppressants, antiviral agents, anesthetics, antiemetics, and antihistamine agents.

14. The composition of claim 13, wherein the hydrophobic drug is selected from the group consisting of paclitaxel, camptothecin, doxorubicin, cisplatin, 5-fluorouracil, cyclosporine A, amphotericin B, itraconazole, ketoconazole, indomethacin, testosterone, estradiol, dexamethasone, prednisolone, and triamcinolone acetonide.

15. The composition of claim 10, further comprising an organic solvent selected from the group consisting of ethanol, acetic acid, lactic acid, glycolic acid, N-methyl-2-pyrrolidone, benzyl alcohol, glycerin, N,N-dimethyl acetamide, propylene glycol, diethyl amine, and mixtures thereof.

16. A method for preparing a hydrophobic drug containing biodegradable polymeric micelle composition capable of solubilizing said hydrophobic drug in a hydrophilic environment to form a solution, comprising the steps of:

1) preparing a mixture containing an amphiphilic block copolymer having a hydrophilic poly(alkylene glycol) component and hydrophobic biodegradable polymer component, a hydrophobic drug, and a poly(ethylene glycol);

2) subjecting the resulting mixture to one step selecting from the group consisting of:
   (a) stirring at 30 to 100° C.;
   (b) stirring at 30 to 100° C. while adding an organic solvent into said mixture; and
   (c) dissolving said mixture in an organic solvent followed by evaporating the solvent.

* * * * *